United States Patent
Huang et al.

(10) Patent No.: US 10,520,444 B2
(45) Date of Patent: Dec. 31, 2019

(54) DEVICE FOR SPECTROSCOPIC DETECTION AND MONITORING OF BIOLOGICALLY RELEVANT MOLECULES

(71) Applicant: The Texas A&M University System, College Station, TX (US)

(72) Inventors: Po-Jung Huang, College Station, TX (US); Gerard L. Coté, College Station, TX (US); Mitchell B. Robinson, Willow Park, TX (US); Jun Kameoka, College Station, TX (US); Haley L. Marks, Brighton, MA (US)

(73) Assignee: The Texas A&M University System, College Station, TX (US)

(*) Notice: Subject to any disclaimer, the term of this patent is extended or adjusted under 35 U.S.C. 154(b) by 28 days.

(21) Appl. No.: 15/975,313

(22) Filed: May 9, 2018

(65) Prior Publication Data
US 2018/0259459 A1   Sep. 13, 2018

Related U.S. Application Data

(62) Division of application No. 15/431,604, filed on Feb. 13, 2017, now Pat. No. 9,989,471.
(Continued)

(51) Int. Cl.
*G01J 3/44* (2006.01)
*G01N 21/65* (2006.01)
(Continued)

(52) U.S. Cl.
CPC ...... *G01N 21/658* (2013.01); *B01L 3/502753* (2013.01); *G01N 1/34* (2013.01);
(Continued)

(58) Field of Classification Search
CPC ..... G01J 3/02; G01J 3/44; G01N 1/34; G01N 21/65; G01N 21/658; G01N 2021/656
See application file for complete search history.

(56) References Cited

U.S. PATENT DOCUMENTS

2003/0089664 A1   5/2003   Phillips
2004/0118771 A1   6/2004   Schukar et al.
(Continued)

*Primary Examiner* — Abdullahi Nur
(74) *Attorney, Agent, or Firm* — Winstead PC

(57) ABSTRACT

There is a need in the point-of-care diagnostic community for an efficient and portable method for testing blood and other biological fluids that can be easily translated across multiple applications. An aspect of the invention described involves monitoring the optical properties of molecularly-mediated nanoparticle assemblies though an optically transparent and magnetically active microfluidic chip, which has recently emerged as an attractive method for biomarker detection as it is an efficient tool for monitoring the binding events that take place in a sensing assay. In one embodiment, this device is directed towards two-nanoparticle assays that rely on the assembly or disassembly of plasmonic and magnetic nanoparticles in response to a certain analyte. A further embodiment is directed to a spiral microfluidic using inertial forces to filter fluid components by size, connected to a magnetically active channel comprised of a nickel micropad array, optically transparent microchannel, and permanent magnets.

8 Claims, 9 Drawing Sheets

Related U.S. Application Data

(60) Provisional application No. 62/294,235, filed on Feb. 11, 2016.

(51) Int. Cl.
| | | |
|---|---|---|
| *G01N 1/34* | (2006.01) | |
| *B01L 3/00* | (2006.01) | |
| *G01N 33/553* | (2006.01) | |
| *G01N 33/543* | (2006.01) | |
| *G01N 1/40* | (2006.01) | |

(52) U.S. Cl.
CPC . *G01N 33/54326* (2013.01); *G01N 33/54346* (2013.01); *G01N 33/54366* (2013.01); *G01N 33/553* (2013.01); *B01L 2300/0654* (2013.01); *B01L 2300/088* (2013.01); *B01L 2300/0816* (2013.01); *B01L 2300/0861* (2013.01); *G01N 2001/4088* (2013.01); *G01N 2021/651* (2013.01)

(56) References Cited

U.S. PATENT DOCUMENTS

2015/0223433 A1* 8/2015 Navawongse ....... A01K 29/005
                                                    119/421
2016/0004298 A1* 1/2016 Mazed .................... G06F 3/011
                                                    345/633

* cited by examiner

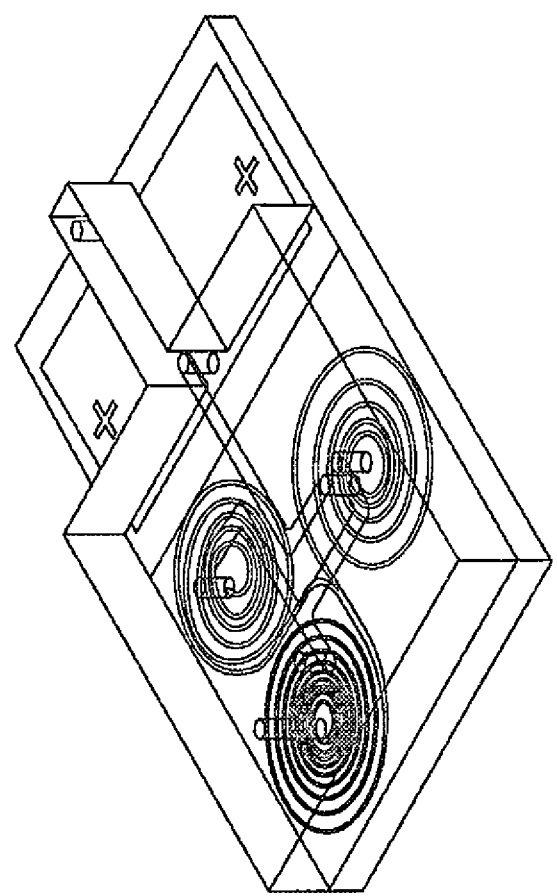
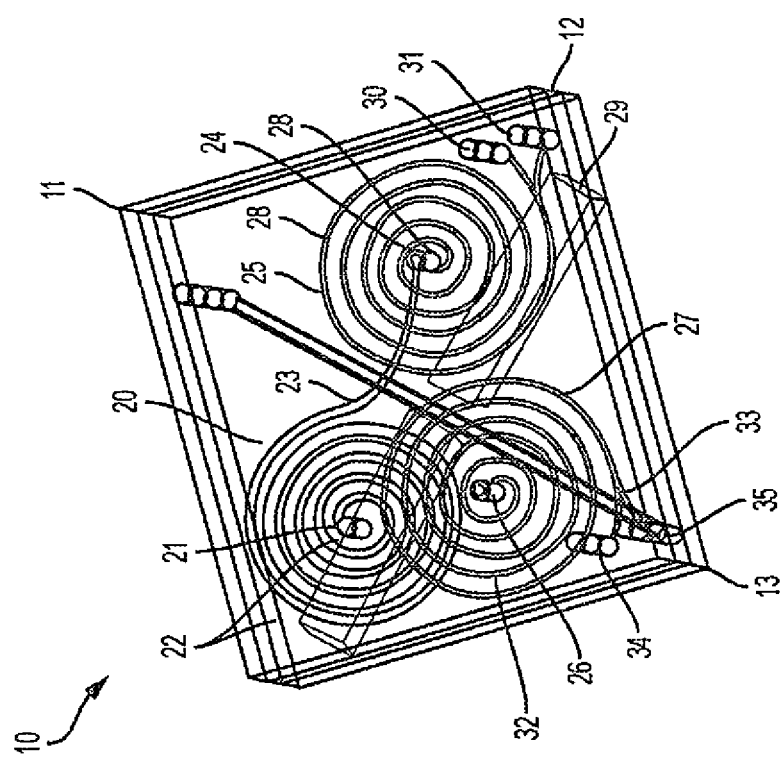
FIG. 1B
FIG. 1A

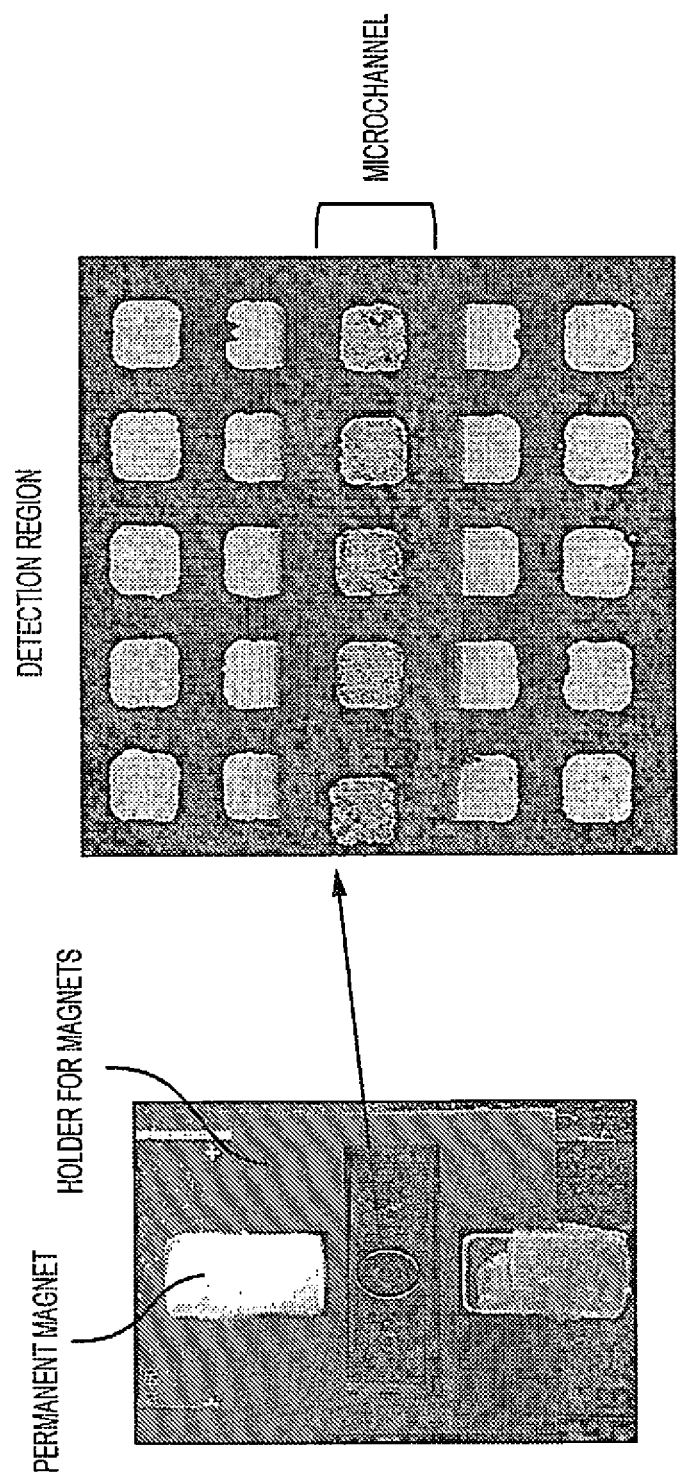

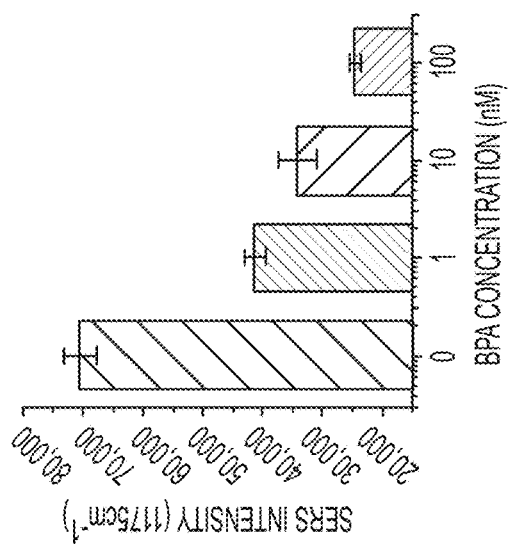
FIG. 8C
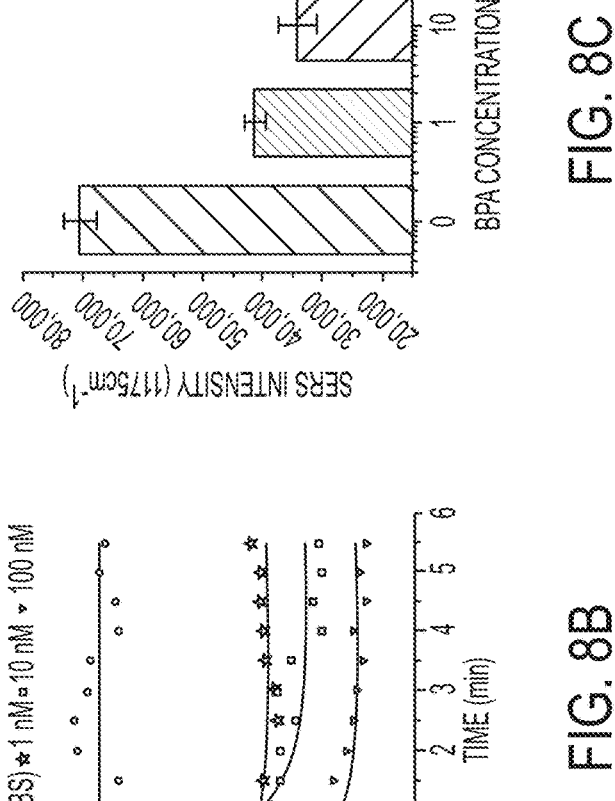
FIG. 8B
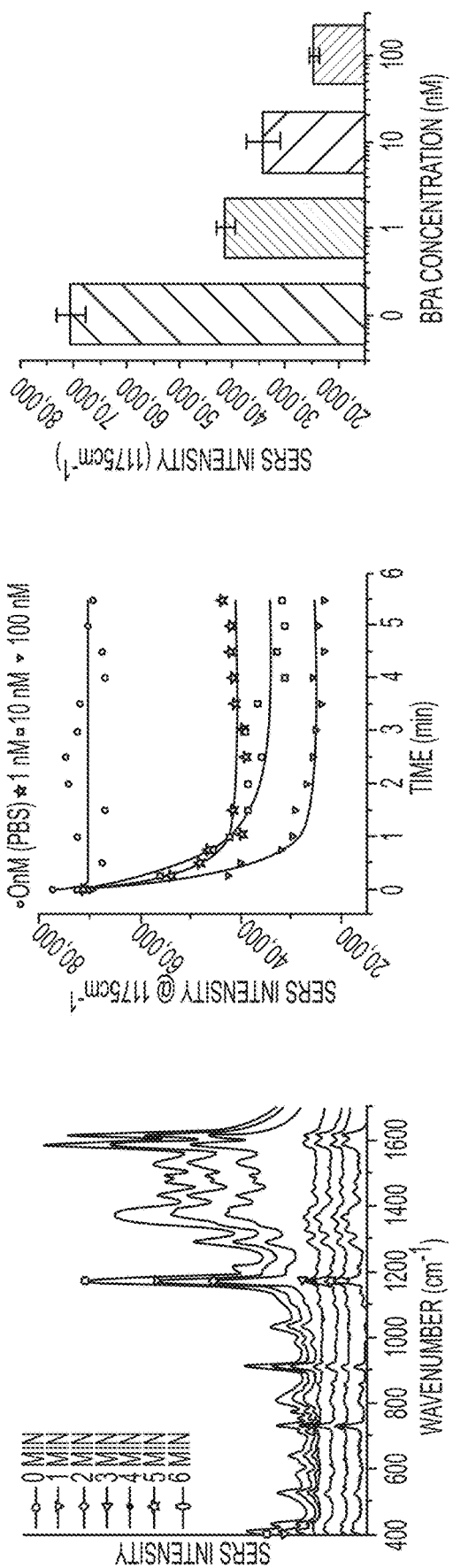
FIG. 8A
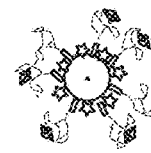
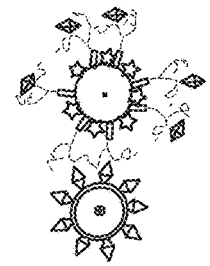
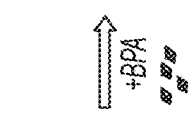
FIG. 8D

DEVICE FOR SPECTROSCOPIC DETECTION AND MONITORING OF BIOLOGICALLY RELEVANT MOLECULES

CROSS-REFERENCE TO RELATED APPLICATIONS

This application is a divisional of application Ser. No. 15/431,604 filed Feb. 13, 2017, which claims the benefit of priority to and incorporates by reference the entire disclosure of U.S. Provisional Patent Application No. 62/294,235 filed on Feb. 11, 2016.

STATEMENT REGARDING FEDERALLY SPONSORED RESEARCH OR DEVELOPMENT

This invention was made with government support under Contract No. 1133512 awarded by The National Science Foundation and Contract No. R43 ES022303 awarded by the National Institutes of Health. The government has certain rights in the invention.

BACKGROUND OF THE INVENTION

Disease-identifying proteins, toxins and carcinogens, bacteria, viruses, cancerous cells, and many other biomarkers can all be found in the circulatory system, making the blood and other bodily fluids a diagnostic goldmine. The CDC estimates that approximately 6.8 billion in vitro laboratory tests are performed annually in the U.S., making them the most commonly performed medical tests. Conversely, 87% of tests must be sent to a centralized hospital or independent laboratory and generally require hours or even days for results due to sample preparation, assay design, and/or logistic delays. Currently most diagnostic assays require complex sample preparation and are sent to central laboratories that require hours or days for results due to sample preparation, assay design, and logistic delays. Separation of small biomarkers from cellular components in biological fluids is specifically critical for accuracy in diagnostic testing as cellular fractions can cause errors and inconsistencies. Poor sample preparation leads to required reprocessing of samples and the subsequent delays lead to poor patient triage in a hospital setting, which in turn can have life-threatening consequences and this type of separation is not convenient in the field or for remote sensing.

Moving towards a lab-on-a-chip system for diagnostic testing offers many advantages such as automated measurement, low sample and reagent volumes, minimal sample preparation, portability, disposability, and user-friendly interfaces. An automated lab-on-a-chip filtration device could help eliminate laboratory delays and results could be analyzed more quickly in the field/at the patient's side and without the risk of human error. Thus, development of a portable, robust, disposable biological fluid separation chip could significantly enhance the realization of a number of developing point-of-care devices with a variety of applications such as remote and emergency health monitoring, pharmaceutical testing, academic research or home test kits.

Lab-on-a-chip type sensors utilizing disposable chip platforms are emerging as a promising technology for detecting and monitoring biomarkers and environmental agents in the blood, urine, saliva, drinking water, and consumable products. A couple systems have been implemented for the most frequently ordered blood tests such as: monitoring electrolytes, metabolites, blood gases, and hematocrits (I-STAT); to detect HIV, syphilis and other infectious diseases (mChip); and to perform up to 25 routine check-up blood panels with one device by combining optical light scatter, colorimetric and electrochemical methods (Ativa). However a number of setbacks arise when designing sensing platforms for detecting more complex or newly emerging biomarkers. This is especially true for small molecules with structures such as foreign toxins, carcinogens, and drugs with low immunogenicity. We aim to solve this by combining our group's assays, which have demonstrated the ability to overcome this issue in the utilization of engineered sensing ligands and signal enhancing nanoparticles for ultra-low limits of detection, with custom optofluidic chips to portably house the assay and provide user-free sample preparation.

Sensing assays discussed herein are easily translatable to virtually any biomarker through the utilization of engineered sensing ligands and signal enhancing nanoparticles for ultra-low limits of detection, with custom optofluidic chips to portably house the assay and provide user-free sample preparation. This technology can potentially be made robust, field portable, and sensitive to other analytes by changing the biorecognition molecule and aptamer—making the platform 'programmable'. Thus the chip platform can potentially be used for a number of applications in situations where rapid blood or other biofluid diagnostics are of critical necessity, such as, for example, for biomarkers for preeclampsia, dengue fever, radiation exposure, blood toxins, or myocardial infarction. Its versatility, low manufacturing cost, and portability also make it a promising technology for global health implications, ambulatory settings, as well as natural disaster relief worldwide. The enablement of technologies like this help push medicine to become increasingly personalized, predictive, and preventative by moving away from initial symptom based diagnostics and towards fast, quantifiable monitoring.

SUMMARY OF THE INVENTION

An embodiment of the invention is directed to a spiral filtering device comprising a first spiral, a second spiral comprising an inlet coupled to the first outlet; and a third spiral comprising an inlet coupled to the second outlet.

A further embodiment of the invention is directed to a magnetic channel-based SERS device comprising a nickel micromagnetic array, a microfluidic channel; and a magnet.

Other embodiments of the invention are directed to a competitive binding type assay utilizing a plasmonic nanoparticle and a metal-coated magnetic nanoparticle for the detection of a body fluid analyte, with one potential embodiment of the assay comprising a target silver nanoparticle functionalized with a Raman reporter dye and PEGylated analyte-binding molecules, wherein the silver nanoparticle is designed to bind to both the free analyte itself as well as a version of body fluid analyte that is in turn PEGylated and immobilized onto the silver coated magnetic nanoparticles, thus initiating binding-mediated assembly of the two particle types and wherein the particles disassemble upon exposure to the free form of the analyte.

Another embodiment of the invention is a method of colloid analysis using a microfluidic chip, with the method comprising of a PDMS microfluidic chip that utilizes the magnetic properties of assay particles to house the particles and monitor their optical response over a micro nickel array, wherein the plasmonic properties of the assay particles multiplies a SERS signal intensity while providing repeatable localization of the assay components.

BRIEF DESCRIPTION OF THE DRAWINGS

FIG. 1A and FIG. 1B illustrate two potential embodiments of the device, comprised of a spiral device for filtering a fluid and microfluidic magnetic device for holding and capturing functionalized nanoparticles concurrently;

FIG. 4A shows a photographic image of a magnetic optofluidic chip; FIG. 4B shows a brightfield microscope image of the detection region under 10× magnification;

FIG. 8A, FIG. 8B, FIG. 8C and FIG. 8D show a SERS spectra of a target and probe nanoparticle assembly NPs before BPA is present (0 min) and the assay response after exposure to 0-100 nM of the competing analyte BPA in free solution (~5 min); and FIG. 9A-1, FIG. 9B-1 and FIG. 9C-1 show brightfield microscope images of three embodiments of Ni-patterned detection regions through a 10× objective; FIG. 9A-2, FIG. 9B-2 and FIG. 9C-2 show Raman color maps of packaged assay particles in the 'SERS on' state.

DETAILED DESCRIPTION OF EXEMPLARY EMBODIMENTS

There is a need in the point-of-care diagnostic community for an efficient and portable method for isolating biomarkers from the larger components of biological samples, such as cellular components. The most commonly used method to remove larger components like cellular components from patient samples is centrifugation, which is traditionally carried out at a dedicated facility, increasing time from the ordering of a test to the generation of a result. Another problem posed by the centrifugation is the possibility of user error, as some cellular components may be extracted with the plasma during pipetting. The use of a passive on-chip inertial microfluidic device could alleviate these issues.

Figure 9D:
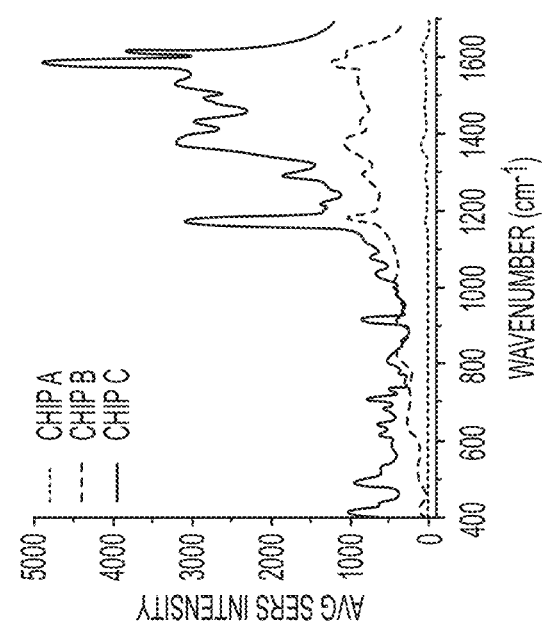
FIG. 9D shows full SERS spectra of the brightest regions of the Raman maps.
Figures 1, 2, 9A:
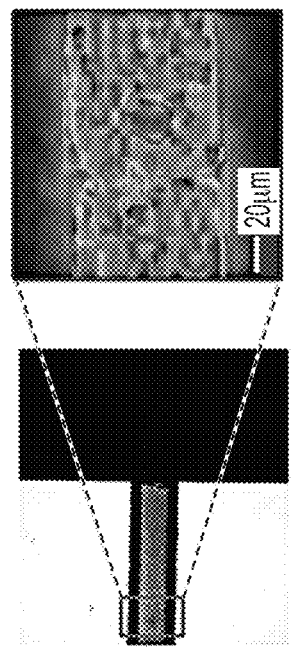
Figures 1, 2, 9B:
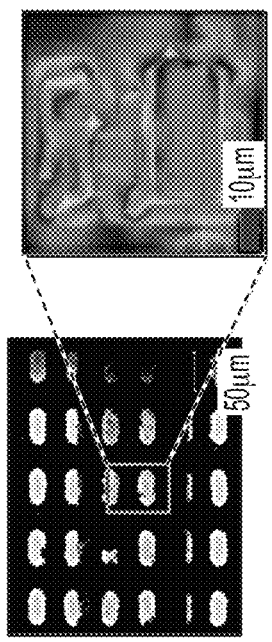
Figures 1, 2, 9C:
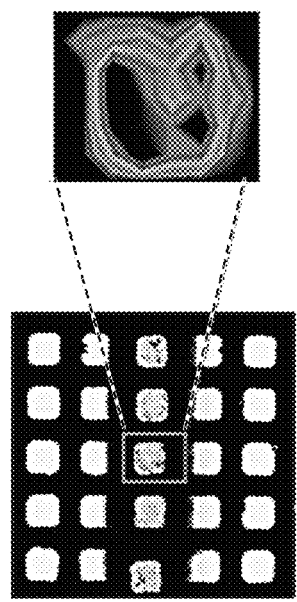

Present spiral microfluidic devices typically contain a single filtering spiral set, leading to the need for a more dilute sample to obtain the same separation results. By increasing the number of spirals in succession (e.g., see the embodiments of FIGS. 1 and 2), the device is able to be more selective and allow for separating higher concentrations of larger particles without dilution that would otherwise be detrimental to filtering efficiency. By selecting appropriate channel widths and heights, our filter is able to be variably selective for different particles based on size in different sections of the filtering spirals. While filtering behavior is partially determined by flow rate and the change in flow rate causes changes in filtering efficiency, our device can be tuned to include additional 'pressure-balancing' spirals to allow for relatively high flow rates, which allows for quicker filtering of samples. Based on these aspects, our device provides a faster, more efficient method for the isolation of relevant biomarkers from biological fluids that can be easily integrated with other lab-on-a-chip platform technologies particularly useful for remote monitoring.

FIGS. 1A-1B demonstrate an exemplary embodiment of a spiral device 10 for filtering a fluid, the microfluidic for holding the preloaded assay and nanoparticles, and a magnet for entrapping the nanoparticles. FIG. 1A is a perspective view of the spiral device 10 that shows each of layers 11, 12, and the bottom layer 13, which includes the microfluidic device (running from the lower right to the upper left) that holds the preloaded assay and nanoparticles as well as the magnetic device that entraps the nanoparticles and includes the two magnets (one in the lower left and a second in the upper right). FIG. 1B is one embodiment of the microfluidic channel with a magnetic capture and hold component that resides in the same layer as the spiral device. In a typical embodiment, the spiral device 10 comprises multiple layers, such as layers 11 and 12, (FIG. 1A). Each layer may comprise one or more features that guide the fluid through the spiral device 10. For example, layer 11 includes a first spiral 20. The first spiral 20 includes an inlet 21, a series of coils 22, and a y-outlet 23. To test the fluid, a user administers the fluid to the inlet 21. The fluid then flows through the series of coils 22 from the inside of the series of coils 22 towards the y-outlet 23. In a typical embodiment, the series of coils includes approximately 5 coils. In other embodiments, the series of coils 22 may be 'tuned' to include more or fewer coils as need to create a desired separation of components within the fluid. As the fluid flows through the series of coils 22, components within the fluid begin to separate due to forces similar to those experienced during centrifugation.

As the fluid reaches the y-outlet 23, the fluid has separated into a first fluid fraction and a second fluid fraction. The first fluid fraction may comprise multiple components (e.g., fluids, solids, and the like). Similarly, the second fluid fraction may comprise multiple components. The first fluid fraction is separated from the fluid and directed to an inlet 24 of a second spiral 25 and the second fluid fraction is separated from the fluid and directed to an inlet 26 of a third spiral 27. The second spiral 25 and the third spiral 27 are disposed within layer 12 of the spiral device 10 so that the inlet 24 and the inlet 26 can receive the first and second fluid fractions, respectively. In some embodiments, two spirals are used to balance resistances to flow. The first and second fluid fractions flow through the second spiral 25 and the third spiral 27, respectively. The second spiral 25 includes the inlet 24, a series of coils 28, and a y-outlet 29. The y-outlet 29 leads to an outlet 30 and an outlet 31. As the first fluid fraction flows through the second spiral 25, the first fluid fraction separates into a third and a fourth fluid fraction. The third fluid fraction is directed to the outlet 30 and the fourth fluid fraction is directed to the outlet 31. The third spiral 27 includes the inlet 26, a series of coils 32, and a y-outlet 33. The y-outlet 33 leads to an outlet 34 and an outlet 35. As the second fluid fraction flows through the third spiral 27, the second fluid fraction separates into a fifth and a sixth fluid fraction. The fifth fluid fraction is directed to the outlet 34 and the sixth fluid fraction is directed to the outlet 35. Each of the third, fourth, fifth, and sixth fluid fractions can then be collected from its corresponding outlet.

The filtered fluid from outlet 35 is then transported down the microfluidic channel from the lower left to the upper right in layer 13 of FIG. 1A. This third layer is the analysis region of the chip. Upon introduction of the analyte from the filtered solution from outlet 35, preloaded non-magnetic silver nanoparticles are competitively unbound and freed from magnetic nanoparticles trapped above the micromagnets causing the surface enhanced Raman spectroscopy (SERS) signal to "turn-off", or rather, a signal decrease is observed in response to the competitive binding event. Alternatively, the sample fluid passes by preassembled functionalized nanoparticles that are immobilized upstream from the magnets and the magnetic particles that are competitively displaced are trapped by the downstream micromagnets causing the SERS signal to "turn on" or rather increase the response signal over the micropads with increased analyte.

It is noted that what is described is a single embodiment and that mechanical aggregation techniques using micro-to-nanochannel configurations could be used instead of using magnetic entrapment. Further, various sensing chemistries including antibodies and aptamers as well as various nanoparticles can be used such as gold and silver spheres, cubes, cages, and core-shell particles.

Figure 2B:
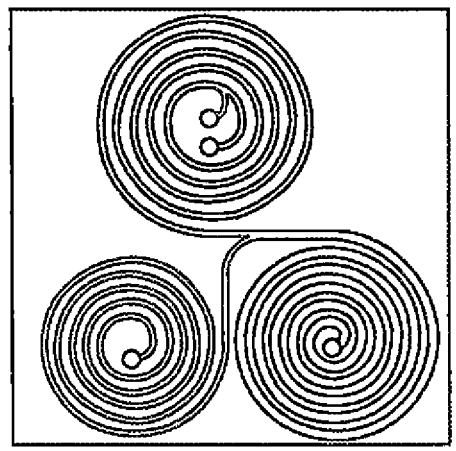
FIG. 2A and FIG. 2B illustrate an embodiment of a spiral device for filtering a fluid.
Figure 2A:
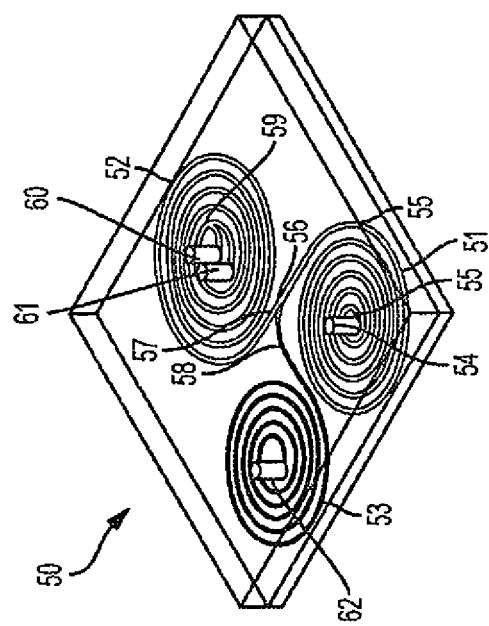

FIGS. 2A and 2B show an exemplary embodiment of a spiral device 50 for filtering a fluid. FIG. 2A is a perspective view of the spiral device 50 and FIG. 2B is a top view of the spiral device 50. The spiral device 50 comprises a first spiral 51, a second spiral 52, and a third spiral 53. The first spiral 51 includes an inlet 54, a series of coils 55, and a y-outlet 56. A fluid for filtering enters the spiral device 50 via the inlet 54. The fluid then flows from the inlet 54 to the y-outlet 56. The y-outlet 56 leads a first fluid fraction of the fluid into the second spiral 52 and a second fluid fraction of the fluid into the third spiral 53.

The first fluid fraction flows to a y-outlet 59, which leads to an outlet 60 and an outlet 61. The first fluid fraction is separated by the second spiral 52 into a third fluid fraction and a fourth fluid fraction. The third fluid fraction is directed to outlet 60 and the fourth fluid fraction is directed to outlet 61. The second fluid fraction flows to spiral 53 to outlet 62. Each of the second fluid fraction, third fluid fraction, and fourth fluid fractions can then be collected from its corresponding outlet.

A prototype comprising a first filtering spiral channel with a width of 500 microns and a height of 50 microns was created. Two subsequent spirals having widths of 250 microns with a height of 50 microns were arranged to be coupled to the first filtering spiral. In the embodiment of FIGS. 2A and 2B, each of the first, second, and third spirals has 5 loops. The inlet is at the center of the first filtering spiral, and, after completing the first spiral, the end of the first filtering spiral splits off into first and second outlets that lead to the second and third filtering spirals. The first outlet leads to an inlet at a center of the second filtering spiral and the second outlet leads to an inlet at a center of the third filtering spiral. The second filtering spiral includes two outlets to further separate cellular components from the plasma (See FIGS. 2A and 2B). From these results we find that the on-chip filtering of cells from other biological fluids for the isolation of relevant diagnostic biomarkers is feasible.

The passive nature of the exemplary spiral devices 10 and 50 allows for consistent filtration without requiring user skill, owing its filtering capability to the geometry of the channels and the velocity of the fluid inside. Additionally, the reduced size of the spiral devices 10 and 50 allows for their integration into a handheld testing system for biological fluid analysis. As a component of a larger testing system, the spiral devices 10 and 50 can be used as the first step for a point-of-care method of biological fluid analysis and can significantly cut down the time and cost compared to outsourcing lab testing. This invention relates to a microfluidic spiral filter device, containing two or more filtering spirals, used for the separation of relevant biomarkers from blood, saliva, urine, and other biological solutions.

Figure 3B:
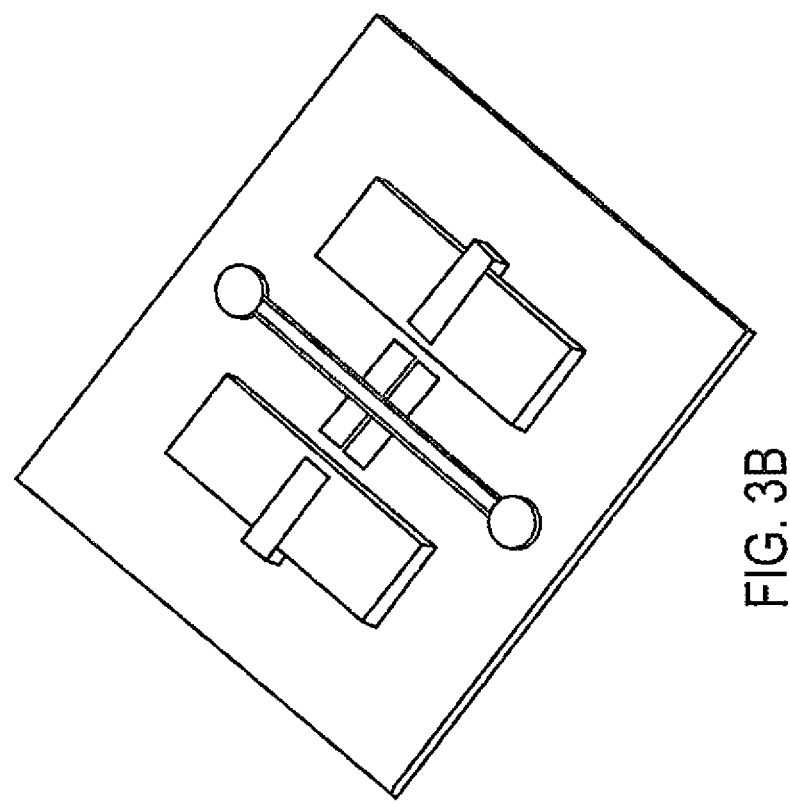
FIG. 3A and FIG. 3B illustrate two embodiments, spotted and straight, of a microfluidic magnetic device for holding and capturing functionalized nanoparticles.
Figure 3A:
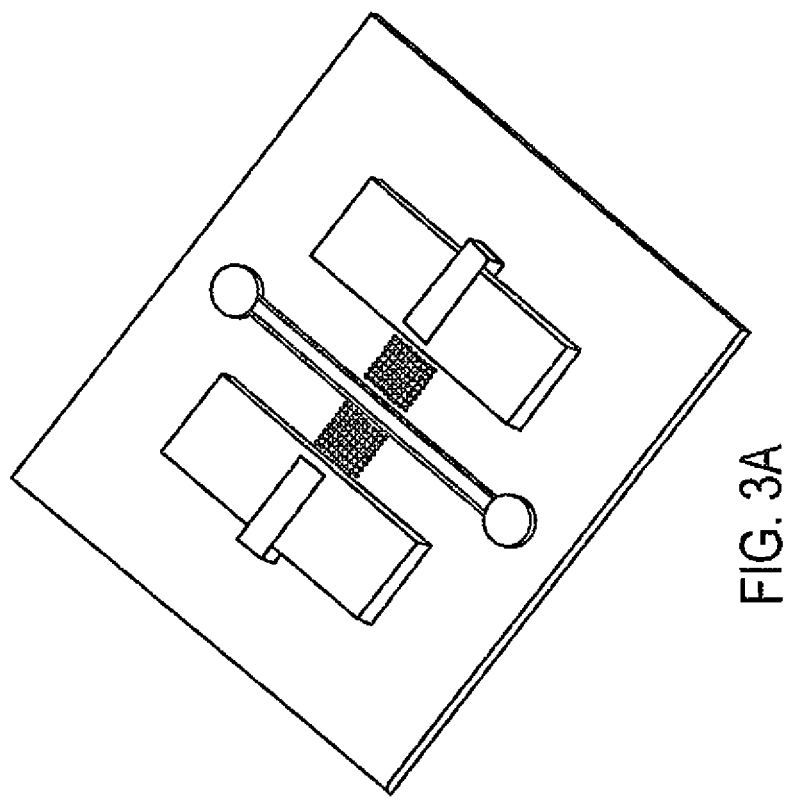

FIG. 3A and FIG. 3B illustrate two embodiments of a microfluidic magnetic device, spotted and straight respectively, for holding and capturing functionalized nanoparticles.

The design of the filter device may be altered by changes to, for example, channel length, width, height, and number of spirals used in tandem to vary the selectivity and functionality of the filter. By carefully tuning the dimensions of the spirals and the speed with which fluids flow through them, the filter device is able to separate, isolate, and concentrate relevant biomarkers from larger components like cellular components in the same fashion as a centrifuge. The microfluidic nature of our device also allows for a small sample of fluid, in the range of tens to hundreds of microliters, and eliminates user error from manual sample preparation. In the case of blood this means the sample can be collected as a droplet from a pricked finger rather than a traditional venous collection site. While the device may be used in isolation, the integration into a point-of-care diagnostic system is where our device could make its biggest impact. As the first step in a microfluidic diagnostic system, our device would reduce the time and cost required to acquire the same results as a traditional off-site testing facilities. The ability to process biological fluids into a diagnostically relevant form in an inexpensive, consistent, and prompt manner makes our device significant for point-of-care diagnostics.

The basic platform comprises the microfluidic device, the sensing chemistry and nanoparticles, and the reader device. In one embodiment, the channel master molds (e.g., spirals/channels of spiral devices 10 and 50) are produced on silicon wafers using soft photolithography techniques and microfluidic devices (e.g., spiral devices 10 and 50) are cast out of polydimethylsiloxane (PDMS), though other materials may be used in other embodiments. For example, the microfluidic device may comprise of one or more of the following materials depending on the embodiment: borosilicate glass, polydimethylsiloxane (PDMS) or other photopolymers, acrylic materials such as poly(methyl methacrylate) (PMMA), and 3D printed plastics. The microfluidic device may also include embedded permanent magnets and/or patterned ferromagnetic materials. The Assay may be comprised of metallic and/or magnetic colloidal nanoparticles that have been functionalized with at least two of the following: an optically active reporter molecule, a sensing ligand such as an aptamer or antibody, a stabilizing agent such as polyethylene glycol (PEG) or polyvinylpyrrolidone (PVP), and the targeted analyte itself (protein, small molecule, bacteria, virus, or other biomarkers of interest). The optical reader may comprise lasers, spectroscopic gratings, filters, and objective lenses.

In some embodiments, the device contains two or more stacked microfluidic chips, where one microfluidic chip is responsible for sample preparation and the other microfluidic chip is responsible for optical analysis of the preloaded nanoparticles' response to a biological fluid. In one embodiment a surface-enhanced Raman spectroscopy (SERS) based competitive binding assay is used in which plasmonic and magnetic nanoparticles are used for detection of analytes including blood toxins, cardiac biomarkers, and/or biomarkers for preeclampsia, dengue fever, radiation exposure, etc.

Operation of one embodiment of the device comprises the following steps: First, blood enters a single spiral filter in the chip's top layer. The outlet of the single spiral filter leads to a second spiral filter. The outlet of the second spiral filter leads to an inlet of a third layer or to a second chip on the same glass slide, which is an analysis region of the chip. Upon introduction of free analyte from the filtered sample such as blood, urine or saliva, non-magnetic silver nanoparticles are competitively displaced and freed from magnetic nanoparticles, which reverses the pre-bound nanoparticle assembly and causes the SERS signal to "turn-off" and decrease in response to the competitive binding event.

Mechanical aggregation techniques using micro-to nano-channel configurations have also been designed, built, and tested instead of using magnetic entrapment. Further, various sensing chemistries including antibodies or aptamers, off-on and on-off configurations, and various nanoparticles have been used such as gold and silver spheres, cubes, cages, and core-shell particles.

Embodiments of each chip have been prototyped and tested separately for one specific embodiment of the overall technology: to detect analytes in blood or other body fluids. Currently, work is ongoing towards integrating these into one stacked chip. Various chemistries, nanoparticles, and micro-nanochannel configurations have been tested.

A prototype PDMS microfluidic chip that utilizes the magnetic properties of the assay particles to house the particles and monitor their optical response in the channel, shows a 10 fold increase in SERS signal intensity while providing repeatable localization of the assay components. Multiple chips can be fabricated on one glass slide, and each chip contains multiple Ni pads embedded within the channel which are magnetically activated by neodymium magnets on either side.

The effects of multiple production methodologies on the separation efficiency of an inertial microfluidic blood filter have been tested and compared. Channel-master molds were produced by microfabrication, using soft photolithography techniques and an SU-8 negative photoresist on silicon wafers, and printing by a stereolithographic 3D printer. All microfluidic devices were cast out of polydimethylsiloxane (PDMS), but many other polymer materials (e.g. PMMA, PEG, etc.), paper-based membranes such as nitrocellulose, or glass materials may be used. Whole blood was pumped through the multispiral microchannels as described above. The absorbance spectra of the outlet solutions were collected and compared for each design as measure of red blood cell separation efficiency.

Prototypes for this device have been developed and have been verified to separate blood cells from blood at a significant level. With sufficiently small channels, the Reynolds number is decreased such that laminar flow takes place exclusively. A channel with curved walls will generate a shift in the flow field, causing what are known as Dean vortices. These vortices push particles of sufficient size toward the inner wall of these curved channels. Testing with our prototype has indicated that with our method, we can remove 99.5% of blood cells from a sample with 2% hematocrit. One embodiment consists of an initial filtering spiral, a second filtering spiral, and a third filtering spiral in parallel with the second filtering spiral to equalize resistances.

The goal is to examine the other possible iterations of the device. For example, iterations include altering the number of spirals and channel dimensions or material to fine tune filtering behavior and quality, as well as developing a systematic approach to analyzing not only blood but other filtered biological fluids.

FIG. 4A shows a photographic image of a magnetic optofluidic chip and FIG. 4B shows a brightfield microscope image of the detection region under 10× magnification.

Optical Assays

Various assays may be used in conjunction with the spiral devices 10 and 50. While a number of nanoparticle based assays exist and have been exhaustively studied, these techniques have not been translated to a commercially viable diagnostic technology. This could be due to difficulties translating traditional enzyme-based assays into a robust lab-on-a-chip devices due to issues with sample preparation and care, or because the persons running the test require some degree of laboratory training and skill. The present invention offers a solution to address these shortcomings in robustness and usability through the utilization of aptamers: high affinity ligands synthesized from short (<100 basepairs) single-strand DNA (ssDNA), which fold into a tertiary structure suitable for binding to a selected analyte of interest. Customized aptamers are conveniently immobilized onto a combination of plasmonic and magnetic nanoparticles and housed within a convenient magneto-optofluidic chip. By controlling and optimizing the magnetic and plasmonic nanoparticle aggregation state and dissociation response to an aptamer's analyte using a lab-on-a-chip platform, there is the ability to provide localized areas of concentrated sensing particles, allowing for more repeatable spectral analyses.

Monitoring the optical properties of molecularly-mediated nanoparticle assemblies has emerged as an attractive methodology for biomarker detection, as spectroscopy of nanoparticles is an efficient tool for monitoring the molecular binding events that take place in a sensing assay. Assays in both "turn-on" and "turn-off" formats have been developed extensively using oligonucleotides to detect DNA fragments, and thus researchers have now begun to explore using aptamers. This would open up the diagnostic capabilities of oligo-nanoparticle assays to the detection of countless biomarkers: from bacterial, fungal, and viral targets, to toxins, neurotransmitters, peptides, and proteins. As this exciting technique for multifunctional biomarker detection progresses, it is also held back by the need for expensive lab equipment and training required to carry out the assay. Our integrated optofluidic sensing device provides a platform methodology for the advancement of successful benchtop techniques, namely the centrifuge and ELISA assay, into a simple lab-on-a-chip technology.

Optical properties of colloidal nanoparticles can be manipulated, tuned, and monitored for plasmonic sensing applications by forcing labeled particles into a controlled, but reversible, aggregative state. Due to the versatility of DNA aptamers, aptamer-mediated surface enhanced Raman spectroscopy (SERS) has recently emerged as an attractive translatable platform method for biomarker detection of virtually any biomarker. Conjugation of aptamers and their corresponding analytes onto plasmonic nanoparticles labelled with a Raman reporter molecule (RRM) mediates the formation of nanoparticle assemblies: molecularly bound bundles of stable colloidal nanoparticles which cause a measurable change in the colloid's overall SERS enhancement of the RRM's Raman spectra. To improve and simplify the detection of the small toxic molecule bisphenol A by its aptamer, multiple plasmonic and magnetic nanoparticle combinations were investigated and the SERS assay response in both a traditional liquid suspension and housed within a microfluidic chip were analyzed and compared.

By controlling and optimizing plasmonic nanoparticle aggregation and monitoring their dissociation responses to an analyte using a microfluidic chip platform, there is the ability to provide localized areas of concentrated sensing particles, allowing for more repeatable analysis. The chip of the present invention is also designed for simple integration with other on-chip devices, such as those for sample preprocessing. Due to the intrinsic properties of colloidal plasmonic nanoparticles it can be used with multiple optical detection schemes such as fluorescence, absorbance, and Raman spectroscopies and can be tuned to virtually any biomarker sensing ligand-pair welcoming continuous innovation after the initial embodiments.

Raman scattering techniques have emerged as a unique tool in the development of blood biomarker assays in providing characteristic chemical fingerprints, low limits of detection, and capability for multiplexing due to narrow band widths. The Raman signal stems from the inelastic scattering of photons by a molecule's electric cloud, providing a chemical fingerprint of the analyte. Only about 1 in 10 incident photons undergoes spontaneous Raman scattering, consequently causing the technique's intrinsically weak signal. In surface enhanced Raman spectroscopy (SERS) electromagnetic enhancements are observed when the analyte is in close proximity to a plasmonic surface such as metallic colloidal nanoparticles. In colloidal SERS, this leads to signal enhancements dependent on inter-nanoparticle distance when the analyte is sandwiched within 1-10 nm of two metallic spherical particles. Nevertheless, SERS techniques utilizing nanoparticles often lack reproducibility and specificity due to the random nature of particle aggregation and the adsorption of interferent molecules onto the metal surface, making it difficult to obtain quantitative analyte information. The integration of SERS detection with biomolecular assays has been recently implemented through the design of SERS nanoprobes: metallic nanoparticles conjugated to molecules with specific optical and biochemical functionalities. SERS nanoprobes require three key conjugated elements: (1) a Raman reporter molecule (RRM) for quantitative identification, (2) a protective element for particle stabilization, and (3) a ligand for assay-specific biorecognition. Strong Raman bands are attributed to RRMs with a high Raman cross section, meaning the molecule's electron cloud is easily distorted by the excitation laser and thus is polarizable. In order to reduce the number of Raman bands for simplified spectral multiplexing, the RRM should also have a low atom count and/or be highly symmetrical. Furthermore, the RRM must provide a functional "head" group for chemisorption to the nanoparticle, most commonly chosen as a thiol (R—SH) for its well-defined covalent attachment to gold. Formation of a self-assembled monolayer (SAM) of RRMs on the nanoparticle surface allows for dense packing of molecules with uniform orientation, improving the reproducibility of the SERS signal. The RRM's terminal "tail" group type also contributes to the dynamics of the nanoparticles as its charge directly affects the total particle surface charge, determining the degree of electrostatic stabilization.

Though a Raman reporter SAM can independently act as the nanoprobe's stabilizing capping agent, additional steric stabilization is often desired for mechanical repulsion between particles. Conjugation of polymers such as poly (ethylene) glycol (PEG) or poly(vinylpyrrolidone) (PVP) to the nanoparticle as part of a mixed SAM, to the RRM's "tail" group, or silica shell encapsulation of the particles drastically improves the colloid's shelf life, even under harsh conditions. Sterically stabilized nanoprobes exhibit minimal nonspecific adsorption and can also provide functionalized surfaces and binding sites for further bioconjugation.

To provide a molecular affinity to the SERS nanoprobe, a biorecognition element (i.e., an aptamer, antigen or antibody) must also be conjugated to a nanoparticle, via a thiol to the gold directly, to another RRM, or to the protective linker. Recently, aptamers, highly specific and sensitive affinity molecules derived from nucleic acids, have been used as SERS nanoprobe recognition ligands in lieu of typical antibodies. Aptamers are specifically advantageous for sensing small molecules with low immunogenicity, where raising antibodies would require synthesis of a hapten-target carrier before animals can be immunized with that conjugate. Selection of aptamers is an entirely in vitro process with the ability to perform counter selection steps and/or selection under non-blood conditions. This provides the potential for greater ligand specificity and affinity, and once identified, aptamers are readily produced by scalable chemical synthesis. Lastly, aptamer terminal functional groups are readily incorporated during synthesis for conjugation to the nanoparticle or other immobilizing molecules.

Aptamers are specifically well-suited for the detection of environmental toxins and carcinogens in the blood, where animal immunizations with certain toxic haptens are not possible or do not trigger an animal immune response, and thus an assay cannot be made without 'piggy-backing' on another antibody, and therefore mass spectroscopy is typically required for the most accurate quantitative results.

As one analyte example, a functional SERS nanoprobe with specific affinity to a BPA-binding aptamer is characterized. The example analyte, Bisphenol A (BPA) in this case, is the monomer of an epoxy resin commonly used in plastic food and beverage packaging, and can be toxic to the endocrine system when exposed to humans. Though environmental monitoring of BPA in the air, water, and the food products themselves is well-established and regulated, there is still a need for reliable human biomonitoring methods in order to determine the body's burden with BPA and its metabolites in the blood. The binding affinity of the nanoprobes and its specificity to the BPA aptamer were quantified using microscale thermophoresis (MST). This approach monitors the signal depletion of a fluorescently labeled aptamer as it moves along an induced temperature gradient. The thermophoresis of molecules is size-dependent, and thus titration experiments are used to quantify the aptamer-nanoparticle binding and determine the dissociation constant Kd. The plasmonic properties of these capture nanoprobes and their capabilities for quantitative SERS detection are also investigated. We demonstrate that the described SERS nanoprobes are capable of acting as both a capture and detecting element for BPA assay development.

Optofluidic Sensor Including Magnetic Control for Nanoparticle-Based Assays

Tests comparing the effects of multiple different methods for magnetic control of plasmonic nanoparticles in a microfluidic were run. The test typically utilized one or more permanent neodymium magnets either embedded in the chip or externally applied. Channel master molds were produced on silicon wafers using soft photolithography techniques, and microfluidic devices were cast out of polydimethylsiloxane (PDMS), though other materials as listed in section 16 may be explored in future embodiments. Our translational assay design protocol for continuous development of the biological assays, which will accompany the chips, relies on the molecularly mediated aggregation, immobilization, and dissociation of plasmonic nanoparticles.

Conjugation of oligonucleotides or DNA aptamers and their selective binding analytes onto metal nanoparticles mediates the formation of nanoparticle assemblies: molecularly bound bundles of nanoparticles which cause a measurable change in the colloid's optical properties that can be detected through the microfluidic chip. In a first embodiment, a "SERS off" competitive binding assay has been developed utilizing plasmonic and magnetic nanoparticles, again as an example, for the detection of the toxin bisphenol A (BPA). The assay scheme involves a 'target' silver nanoparticle functionalized with a Raman reporter dye and PEGylated BPA-binding DNA aptamers. A version of the toxin BPA, bisphenol A diglycidyl ether (BADGE), is PEGylated and immobilized onto a silver coated magnetic 'probe' nanoparticle. When mixed, target and probe nanoparticles cluster into dimers and trimers and an enhancement in the SERS spectra is observed. Assay clusters are loaded into the optofluidic chip previously described, and are trapped over nickel pads patterned within the PDMS channel. Upon introduction of free BPA in its native form, the bound target AgNPs are competitively unbound and freed; reversing the nanoparticle assembly and causing the SERS signal to "turn-off" and decrease in response to the competitive binding event.

Several prototypes for this device have been developed and tested in parallel with the characterization of biological assays. Design parameters for the channels are tuned to the specifics of each assay. Namely, our initial prototype utilizes magnetic and metallic particles functionalized for the detection of the example target analyte bisphenol A (BPA), analyzed by Raman spectroscopy and housed within a disposable PDMS and nickel microfluidic chip.

A PDMS microfluidic chip has been developed that utilizes the magnetic properties of the particles to house this assay, resulting in a 10 fold increase in SERS signal intensity while providing repeatable localization of the assay components. Multiple chips can be fabricated on one glass slide, and each chip contains multiple Ni pads embedded within the channel which are magnetically activated by neodymium magnets on either side.

A goal is to examine the optofluidic assay chip's performance using real biological samples doped with relevant biomarkers and common interferents. In the long term, different iterations of the device will be tested by altering the assay itself for new biomarkers, altering the nanoparticle size, shape, material, or aggregation methodology to tune their signal to different optical systems, and/or altering the channel dimensions, materials, and flow parameters, in order to develop a systematic approach to analyzing the assay response.

Figure 5A:
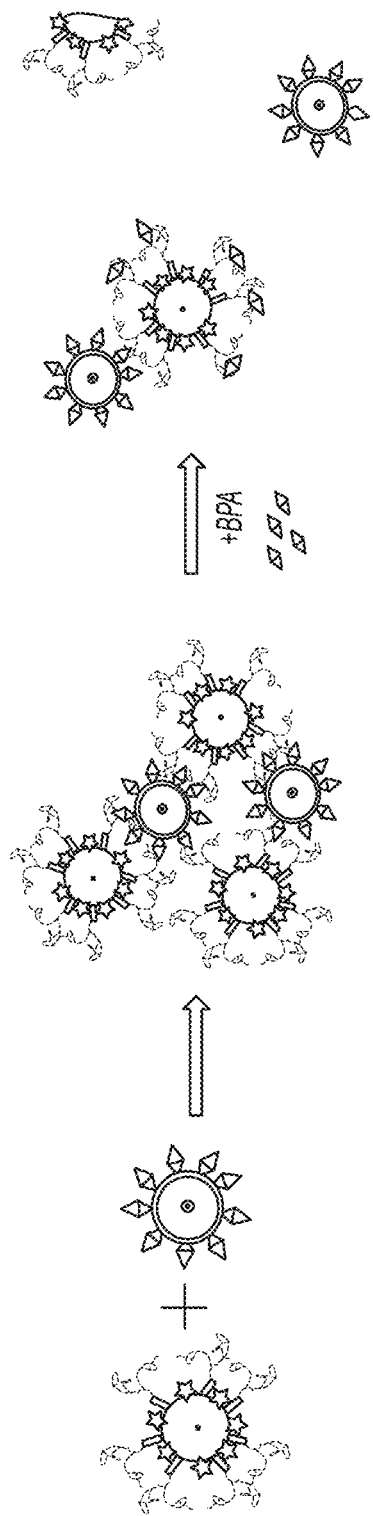
FIG. 5A shows a schematic illustration of the aptamer mediated 'turn-off' SERS competitive binding assay.
Figure 5B:
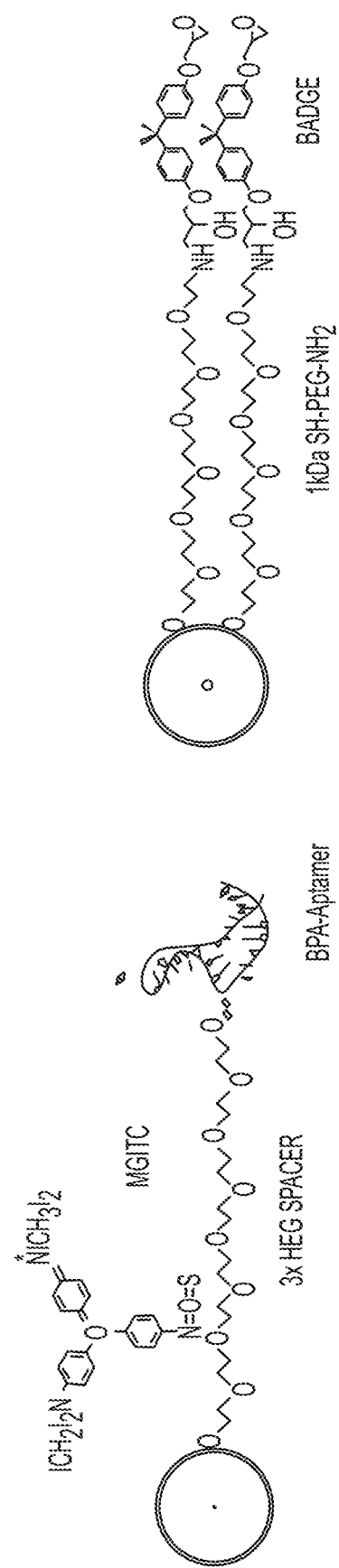
FIG. 5B shows target and probe nanoparticle conjugate components.

Herein the optimization of a "SERS off" competitive binding type assay is presented utilizing a plasmonic silver (AgNP) and silver coated magnetic nanoparticle (Ag@MNP), again for the detection of the example analyte toxin bisphenol A (BPA). FIG. 5A shows a schematic illustration of the aptamer mediated 'turn-off' SERS competitive binding assay; and FIG. 5B shows target and probe nanoparticle conjugate components. The assay scheme shown in FIGS. 5A and 5B involves a 'target' AgNP functionalized with the Raman reporter dye malachite green isothiocyanate (MGITC) and PEGylated BPA-binding DNA aptamers. These particles are designed to bind to a version of the toxin bisphenol A diglycidyl ether (BADGE), PEGylated and immobilized onto a second silver coated magnetic 'probe' nanoparticle, where binding affinities have been determined previously. When mixed, target and probe nanoparticles cluster into small colloidal networks, providing a localized 'hot spot' of electric field enhancement around the RRMs at the nanoparticle interface, and therefore an increase in the number of scattering events experienced by the Raman reporter, observable as an increase in the SERS spectral intensity. This "SERS on" spectral enhancement can then be quantifiably reversed, i.e. "turned-off", by introducing free BPA to the system to compete with the aptamer BADGE interaction, causing the assemblies to release the MGITC-tagged non-magnetic target AgNPs. The assay was first characterized in on and off mode in a standard microwell plate, where assay particles are suspended in solution without magnetic manipulation. Finally $Fe_2O_3$ and $Fe_2CoO_4$ were coated in silver and tested as magnetic cores for the probe nanoparticle, where particles are housed in microfluidic chips capable of magnetically localizing the assay clusters within a PDMS channel.

Materials and Instrumentation

The modified BPA aptamer was synthesized by Integrated DNA Technologies (USA). Hetero-bifunctional PEG linker (NH2-PEG-SH, 1 kDa) was purchased from NanoCS (USA). Malachite green isothiocyanate (MGITC) reporter dye was purchased from Invitrogen (UK). All other reagents were obtained from Sigma Aldrich (USA/UK).

A Varian Cary 300Bio UV-Visible Spectrophotometer was used with a scan range of 200-800 nm for extinction measurements. The zeta potential and hydrodynamic diameters of the nanoparticles were measured on a Zetasizer Nano ZS90 (Malvern, U.K.). All microplate Raman and SERS spectra were collected using a ThermoScientific DXR Raman confocal microscope with a 900 g/mm grating. SERS mapping of the microfluidic channels was done using a WITec Alpha 300R confocal Raman instrument (WITec GmbH, Ulm Germany) with a 600 g/mm grating, fitted with a piezo-driven XYZ scan stage. All samples were probed using a laser wavelength of 532 nm and coupled to a thermoelectrically cooled charge-coupled device (CCD).

Colloid Synthesis

Silver colloid (AgNP) was synthesized using the method reported by Leopold and Lendl. Hydroxylamine hydrochloride (1 ml, 150 mM) was added to 89 mL of NaOH (3.33 mM) under vigorous stirring. Silver nitrate ($AgNO_3$) solution (10 mL, 10 mM) was added drop-wise and stirred for 15 min at room temperature. DLS measurements revealed an average particle diameter of ~45 nm and the stock particle concentration was determined to be 225 pM according to Beer's Law using an extinction coefficient of $2.87 \times 10^{10}$ $M^{-1}$ $cm^{-1}$ at 404 nm.

Silver-coated ferrite nanoparticles ($Ag@Fe_2O_3$) were prepared using a co-precipitation method for the synthesis of the particle core and glucose reduction to coat with silver as described by Kumar et al. and Mandal et al. respectively. Briefly, a stock solution of maghemite ($\gamma$-$Fe_2O_3$) nanoparticles was prepared by adding 25 mL of an acidified iron salt solution (0.4 M Fe2+, 0.8 M Fe3+, 1 M HCl) drop-wise to 250 mL of 1.5 M NaOH at 50° C. under vigorous non-magnetic stirring. After 20 minutes the particles were allowed to cool, washed twice with DI water and once with 0.1M HNO3. An additional 125 mL of HNO3 was then added to the solution, stirred an additional 40 min at 95° C., and re-suspended in distilled water. To coat with silver, 1 mL of these stock MNPs was mixed with 4 mL of 0.35 M glucose and 1.5 mL of 60 μM $AgNO_3$. The solution was sonicated for 10 min then heated to 90° C. for 90 min. Finally, the particles were centrifuged three times to wash, and redispersed in 6 mL of 5 mM sodium citrate for a particle diameter of ~70 nm and final concentration of 425 pM.

Figure 6:
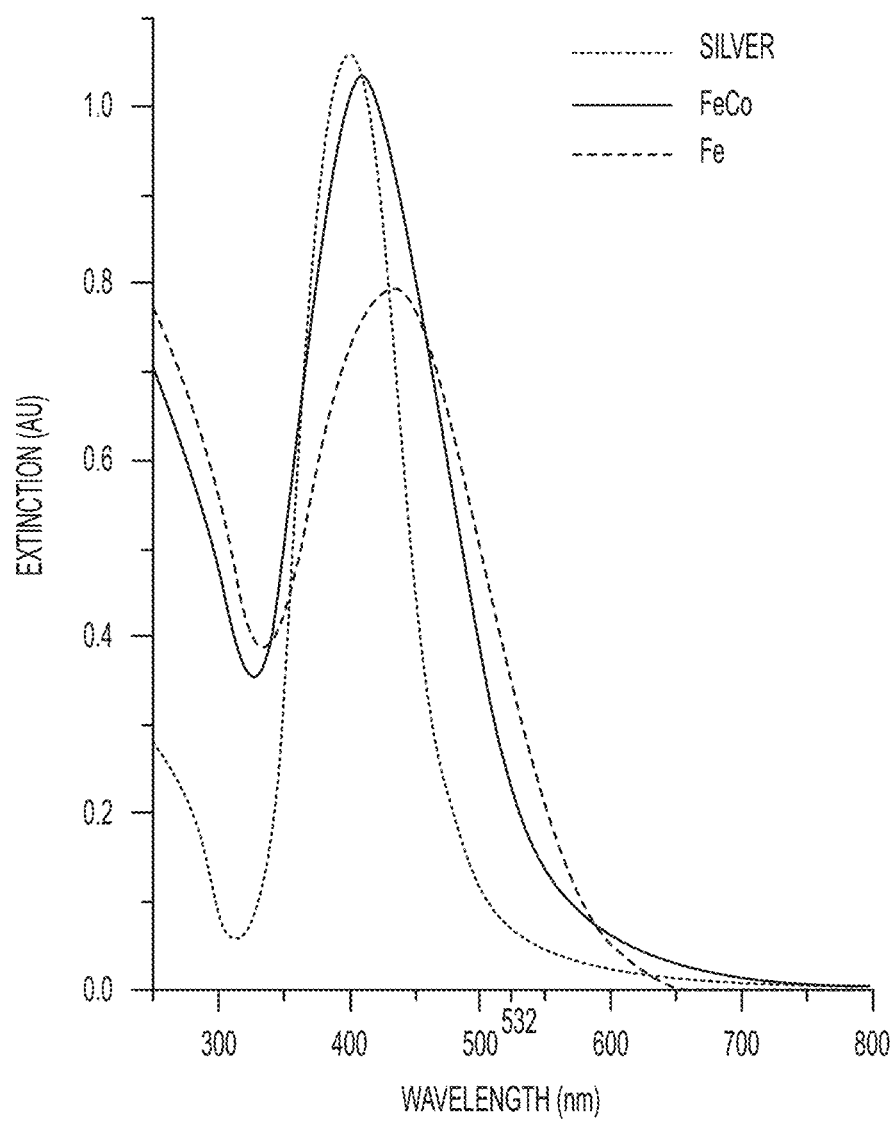
FIG. 6 shows a comparison of the extinction profile of Fe (dashed line) and FeCo (solid line) core nanoparticles after coating with silver, with the solid silver target nanoparticle spectra for reference (dotted line)

Silver-coated cobalt ferrite nanoparticles ($Ag@Fe_2CoO_4$) were prepared by first synthesizing a stock solution of the core $Fe_2CoO_4$ nanoparticles through co-precipitation of iron (III) chloride (0.2 M $FeCl_3$) and cobalt(II) chloride (0.1 M $CoCl_2$) in sodium hydroxide solution at pH ~12 (3.0 M NaOH) using a method modified from Rutirawut et al. The cobalt ferrite salt solution was added rapidly into 3.5 M NaOH solution under vigorous stirring, then headed at 80° C. for 1 h. The cobalt-iron oxide precipitated colloid was washed with deionized water in triplicate using a permanent neodymium magnet. To coat with silver, 500 μL of these stock MNPs was mixed with 4 mL of 0.35 M glucose and 1.5 mL of 60 μM $AgNO_3$. The solution was sonicated for 10 min then heated to 90° C. for 90 min. Finally, the particles were centrifuged three times to wash, and finally redispersed in 6 mL of 5 mM sodium citrate for an average particle diameter of ~35 nm and final stock concentration of 385 pM. The extinction profile of the $Ag@Fe_2CoO_4$ is compared to that of $Ag@Fe_2O_3$ in FIG. 6 along with a silver standard for reference.

Target and Probe Nanoparticle Conjugation
Aptamer/RRM AgNP Target Synthesis

Prior to immobilization, the BPA aptamers were suspended in a 60 mM phosphate buffer (PBS, pH 8.5) and treated with 15 mg of dithiothreitol (DTT) to reduce their disulfide bonds. After 1 h the aptamers were purified using a Nanoseps 10 kDa desalting column to remove residual DTT, and then heated to 90° C. for 5 min to allow the aptamers to fold into their tertiary structure for optimal binding.

Target AgNPs were functionalized with aptamers. The aptamer (7 μM) was added to 1 mL of silver colloid (145 pM) at a molar ratio of 2000:1 and left for 1 h. Three 20 μL aliquots of 250 mM citrate HCl buffer (pH 2.9) were then added 5 min apart, and the sample was left an additional 30 min before centrifuging and re-suspending the aptamer functionalized particles in 1 mL of 0.3 M PBS (pH 7.4). The Raman reporter molecule, malachite green isothiocyanate (MGITC, 10 μM in methanol), was then added at a 500:1 ratio and left to react with the aptamer AgNPs under sonication for 1 h, which were then centrifuged and stored in a 0.1 M PBS buffer (pH 7.4).

Analyte Ag@MNP Probe Synthesis

To synthesize 1 mL of BADGE functionalized magnetic nanoprobes, the SH—PEG—$NH_2$ linker was added drop-wise to an excess of the analyte BADGE in 0.3 M PBS buffer (pH 8.5) and left overnight to allow conjugation between their terminal amine and epoxide groups respectfully. The conjugates were then treated with aminoethanol to open unbound epoxide rings and prevent non-specific binding of BADGE to the RRM's amine groups. These SH-PEG-BADGE conjugates were then added at a 5000:1 ratio to 1 mL of silver coated magnetic nanoparticles (stocks diluted to 225 pM). After 1 h three 20 μL aliquots of 250 mM citrate HCl buffer were again added 5 min apart, and the sample was left an additional 30 min before centrifuging and re-suspending the BADGE functionalized particles in 1 mL of 0.1 M PBS (pH 7.4).

Fabrication of Ni-Patterned Magnetic Microchannel

The magnetic channel-based SERS device is composed of a nickel micromagnetic array. The Ni-micromagnetic array is constructed on a glass slide through lithography using a methodology derived from Ilievski et al. Glass slides are spin-coated with LOR 3A and S-1813 lift-off resists at 750 nm and 1.3 μm, respectively. After exposure and development, the pattern of the Ni-micromagnetic array is visibly transferred onto the glass slides. Next, 100 nm-thick chromium and 50 nm-thick copper are continuously deposited on the pattern as the adhesion layer and then 200 nm-thick nickel is deposited as the 3rd and final magnetic response layer. After deposition, the entire glass slide is placed into the chemical stripper of LOR 3A at 80° C. in order to remove the photoresist layer. A 100 um-thick microfluidic channel mold is constructed on a silicon wafer mold via soft lithography. Uncured PDMS solution (10:1) is poured over the silicon wafer mold and cured at 65° C. for 2 hours as per typical soft lithography methods. Lastly, the PDMS microfluidic channel is bound to the glass slide patterned with a micromagnet array by plasma etching treatment. The nickel pads within the channel are not magnetically activated until the final 3D printed neodymium magnet holder is placed around the channel.

SERS Analysis of Assay in a Microwell

A solution containing equal volumes of 225 pM of each of the target and probe nanoparticles was monitored with SERS for 5 h to allow complete binding between the immobilized BPA aptamers and BADGE. The assembled nanoparticle clusters were collected using a neodymium magnet held at the side of the glass vial, the supernatant containing any unbound AgNPs was removed, and the assembled nanoparticles were re-suspended in 0.1 M PBS (pH 7.4). SERS measurements were collected with the target AgNP concentration held constant at 75 pM in a total volume of 30 μL of 0.1 M PBS (pH 7.4) with an integration time of 10 s (1 s exposure). For competitive binding analysis 10 μL of the assembled target/probe NPs was mixed with 10 μL of 1 μM BPA in and 10 uL of BPA (1 pM to 1 uM) in 0.1 M PBS (pH 7.4) and SERS measurements were taken every 30 s.

SERS Analysis of Pre-Bound Assay Particles in a Magnetic Microfluidic Chip

A solution containing equal volumes of 225 pM of each of the target and probe nanoparticles in a total volume of 300 uL was allowed to flow through the Ni-patterned magnetic channels at a flow rate of 10 μL/min, and sub-sequentially left overnight. The SERS profile of the localized assembled nanoparticle clusters was mapped using WiTec analysis software. Specifically SERS measurements were collected with an integration time of 1 s (1 s total exposure) and a step size of 10 μm for a total 3D mapping area of 150×150×250 μm.

The target nanoparticles were functionalized as described and yielded average zeta potential measurement of −39.7 mV. Probe particles of the Fe and FeCo varietals were found to be −32.1 mV and −22.7 mV respectively, indicating that the PEG spacer and the HEG modified aptamer provide adequate particle stabilization in the 0.1 M PBS binding buffer, but that the Co doped particles were slightly less stable. The intrinsic SERS signal of a stock solution of the assembled nanoparticles as it and its response to the presence of competing BPA was then analyzed in a microwell using the Ag@Fe particles. As shown by FIG. 7, the SERS signal of the reporter molecule MGITC increases by 25 orders of magnitude as it experiences an enhancement in the electric field intensity of its immediate environment due to the aptamer-binding induced particle aggregation, reaching a steady-state equilibrium after ~2 h.

Figure 7A:
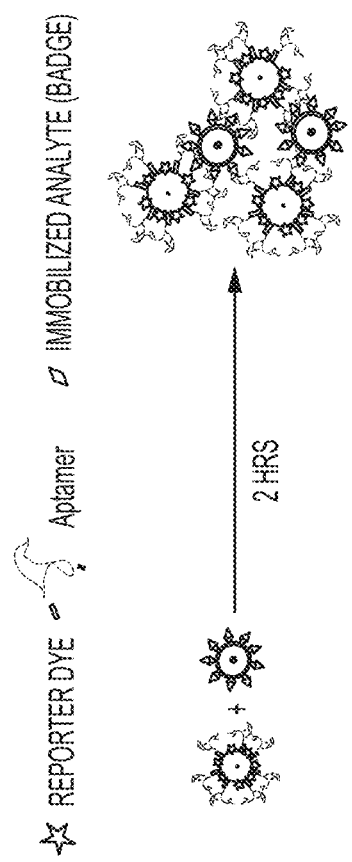
FIG. 7A and FIG. 7B shows the SERS spectral intensity of the 1075 $cm^{-1}$ Raman mode from a target nanoparticle, conjugated to either a BPA specific or nonspecific aptamer sequence, monitored for 5 h after exposure to the probe nanoparticles at a 1:1 molar ratio, with assembly saturation occurring after ~2 h.
Figure 7B:
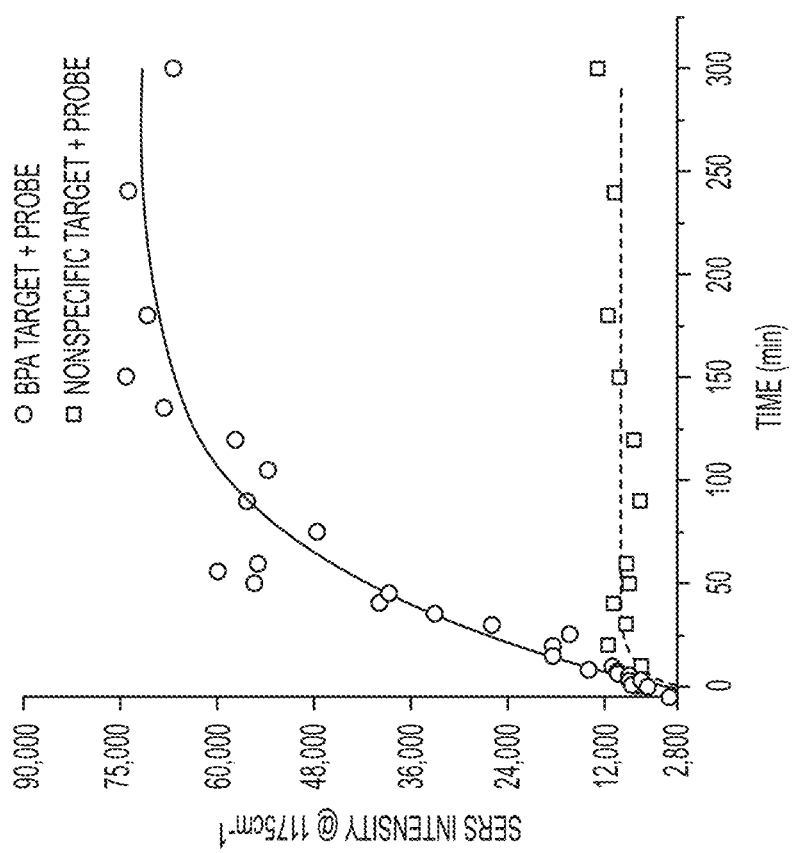

FIG. 7A and FIG. 7B shows the SERS spectral intensity of the 1075 $cm^{-1}$ Raman mode from a target nanoparticle, conjugated to either a BPA specific or nonspecific aptamer sequence, monitored for 5 h after exposure to the probe nanoparticles at a 1:1 molar ratio, with assembly saturation occurring after ~2 h When free BPA is added to the enhanced conjugate solution, it is observed that the SERS intensity of MGITC's 1175 cm−1 peak (aromatic C—H bending vibrational mode) decreases to a steady state over the course of ~3 min as competitive binding occurs (e.g., see FIG. 8). This implies that the BPA aptamer immobilized on the target AgNPs loosens or releases from the BADGE on the MNPs in order to more favorably bind to free BPA, causing a decrease in the solution SERS signal due to MGITC being displaced further from the nanoparticle surface interface as hypothesized.

FIG. 8A, FIG. 8B, FIG. 8C and FIG. 8D show a SERS spectra of a target and probe nanoparticle assembly NPs before BPA is present (0 min) and the assay response after exposure to 0-100 nM of the competing analyte BPA in free solution (~5 min)

In order to create a more repeatable Raman analysis platform for assays relying on magnetic nanoparticles a magnetically activated Ni-patterned optofluidic chip was used to house the sensing chemistry. Specifically, the magnetic collection rate and the SERS enhancement of silver coated $Fe_2O_3$ and $Fe_2CoO_4$ nanoparticles were monitored for three different Ni-pattern designs shown in FIG. 9. Using 3D Raman mapping (FIG. 9A-2, FIG. 9B-2 and FIG. 9C-2), it was found that the straight channel (Chip A; also see FIG. 3A) provided a more uniform nanoparticle organization with a coefficient of variation of 10-20% compared to ~35% variation across the ten Ni-pads within the channel walls (Chip B; also see FIG. 3B). On a positive note, the spotted channels demonstrated a larger SERS enhancement, and thus a lower limit of detection. Further while investigating the error across each individual pad it was discovered that the error could be reduced through normalization to the pads' maximum intensity, for an improved % error in the 10-20% range. Additionally, the $Ag@Fe_2O_3$ particles were, on average, more uniform in size and more stable than $Ag@Fe_2CoO_4$. However the addition of cobalt did significantly improve the collection time of particles from several hours down to ~20 minutes within the magnetic chips and thus may still be worth investigating further. To overcome the issues with chip designs A and B, a more optimized Chip C was created involving a 1×5 array of magnetically activated pads housed within the PDMS channel. When the channel is filled with dried assay particles, Chip C demonstrated SERS enhancements up to five times higher than Chip B and 30 times higher than Chip A as demonstrated by comparing their averaged full spectra over the nickel patterns in FIG. 9D.

An embodiment of the invention is directed to a "turn-off" SERS assay platform methodology for the detection of small toxins utilizing aptamer-mediated assembly of SERS active colloidal nanoparticles. The colloidal SERS assay is formed through the mixing of probe and target nanoparticles and reaches an equilibrium after ~2 hours. This is followed by being able to monitor a three minute competitive binding event initiated by the presence of as little as 10 μL, of 1 nM bisphenol A in free solution. It was determined that the probe nanoparticles have specific preference for the BPA aptamer target particles, and that the particles competitively bind with free BPA as well, implying that no nonspecific binding occurred. This approach has the potential to be translated to any aptamer/antigen pair and provides the added benefit of magnetic manipulation of the nanoparticle sensing network to remove any unbound nanoparticles that could potentially interfere with the Raman readout.

The magnetic microfluidic chip of the present invention is designed for simple integration with other lab-on-chip devices, such as those for sample pre-processing for biological fluids. It has been found that the $Ag@Fe_2O_3$ particles were, on average, larger yet more uniform in size and more stable than $Ag@Fe_2CoO_4$, while the addition of cobalt significantly improved the collection time of particles within the magnetic chips. Using 3D Raman mapping, it has been found that the straight channel design with the $Ag@Fe_2O_3$ particles intrinsically provided the most uniform nanoparticle organization, while the spotted channel design with $Ag@Fe_2CoO_4$ particles demonstrated a larger SERS enhancement, and thus a lower overall limit of detection. It was found that the pad to pad variability could be reduced through normalization to the maximum intensity within a pad, and thus the spotted design used in conjunction with the $Fe_2O_3$ magnetic core varietal of the probe nanoparticle was the most successful iteration of the experiment. Due to the intrinsic properties of colloidal plasmonic nanoparticles this platform technology could potentially be used with multiple optical detection schemes such as fluorescence, absorbance, and Raman spectroscopies and can be tuned to virtually any biomarker-sensing ligand pair-welcoming continuous innovation after these initial embodiments.

While the present invention has been described in terms of certain preferred embodiments, it will be understood, of course, that the invention is not limited thereto since modifications may be made to those skilled in the art, particularly in light of the foregoing teachings.

What is claimed is:

1. A magnetic channel-based SERS device comprising:
   a nickel micromagnetic array, wherein the nickel micromagnet array is constructed on a glass slide through a lift off process;
   a microfluidic channel; and
   a magnet.

2. The device of claim 1, wherein the magnet is a permanent magnet or an electromagnet.

3. The device of claim 1, wherein the microfluidic channel is comprised of polydimethylsiloxane (PDMS) or polyethylene glycol, or a combination of the two.

4. The device of claim 1, wherein the microfluidic channel is comprised of polymethylmethacrylate (PMMA).

5. The device of claim 1, wherein the microfluidic channel is comprised of borosilicate glass.

6. A method of fluid analysis using a microfluidic chip, the method comprising:
   using a microfluidic chip that utilizes magnetic properties of assay particles to house the particles and monitor their optical response on a micro nickel array, wherein the magnetic properties of the assay particles multiplies a SERS signal intensity while providing repeatable localization of the assay components.

7. The method of claim 6, wherein multiple optically transparent microfluidic chips are fabricated on one glass slide, and wherein each microfluidic chip contains multiple micro scale nickel pads embedded within the channel and are magnetically activated by neodymium magnets on either side.

8. The method of claim 7, further comprising stacking or cascaded microfluidic chips to form a double layer modified version, so that an inlet of the a second microfluidic chip aligns with an outlet of a first microfluidic chip for continuous flow and user-free analysis.

* * * * *